(12) United States Patent
Harwood

(10) Patent No.: US 6,502,261 B1
(45) Date of Patent: Jan. 7, 2003

(54) PATIENT SUPPORT

(75) Inventor: William R. Harwood, West Sussex (GB)

(73) Assignee: Elekta AB, Stockholm (SE)

( * ) Notice: Subject to any disclaimer, the term of this patent is extended or adjusted under 35 U.S.C. 154(b) by 0 days.

(21) Appl. No.: 08/983,421

(22) PCT Filed: May 15, 1997

(86) PCT No.: PCT/IS97/00557

§ 371 (c)(1),
(2), (4) Date: Jan. 14, 1998

(87) PCT Pub. No.: WO97/42876

PCT Pub. Date: Nov. 20, 1997

(30) Foreign Application Priority Data

May 15, 1996 (GB) ............................................. 9610129

(51) Int. Cl.[7] .............................. A61B 6/04; A61G 13/06
(52) U.S. Cl. ............................... 5/611; 5/601; 378/209; 108/145
(58) Field of Search ............................... 5/11, 601, 611; 378/209; 254/10 B, 10 C; 108/145

(56) References Cited

U.S. PATENT DOCUMENTS

| 1,631,888 A | * | 6/1927 | Pow | .......................... 5/611 X |
| 3,253,817 A | * | 5/1966 | Lauterbach | ................. 5/611 X |
| 3,302,971 A | * | 2/1967 | Lory | ...................... 108/145 X |
| 3,797,819 A |   | 3/1974 | Platz et al. |   |
| 4,650,143 A |   | 3/1987 | Kurrasch |   |
| 5,013,018 A | * | 5/1991 | Sicek et al. | .................. 5/610 X |
| 5,149,074 A |   | 9/1992 | Jardin |   |
| 5,299,334 A | * | 4/1994 | Gonzalez | ................... 5/610 X |
| 5,410,767 A |   | 5/1995 | Barud |   |
| 5,953,776 A | * | 9/1999 | Sanders et al. | ............. 5/611 X |

FOREIGN PATENT DOCUMENTS

| DE | 4011644 | 10/1991 |
| SE | 503360 | 9/1992 |

* cited by examiner

Primary Examiner—Michael F. Trettel
(74) Attorney, Agent, or Firm—Kinney & Lange, P.A.

(57) ABSTRACT

A patient support 2 comprises two arms 10, 12 pivotally connected together and which extend between a base 6 and a support 14 to which a patient support table is coupled. In the preferred form, each arm 10, 12 comprises linkages which define pivot points 20A to 20D and 30A to 30D forming parallelograms. This ensures the support 14, and hence the table, has a constant orientation relative to the base. The arms 10, 12 may be controllable independently.

20 Claims, 6 Drawing Sheets

PATIENT SUPPORT

This invention relates to patient supports, as may be used, for example, in radiotherapy treatment or diagnostic apparatus.

Various types of patient support are known for use with radiotherapy treatment apparatus, or with X-ray or Magnetic Resonance Imaging systems, and typically comprise a table on which a patient is positioned and a mechanism for adjusting the position of the table. For some applications, it is desired that the patient support table is moveable in the plane of the table so that the patient can be step-wise or continuously driven through an area of the apparatus. This may be desirable for diagnostic, imaging or treatment procedures. Furthermore, it is normally necessary for the table to be situated at approximately 1 m or 120 cm above the ground during the treatment or diagnostic procedure, so that the treatment or imaging head can follow a continuous arc around the patient. This requires the imaging or treatment head to be able to pass beneath the patient support table and thereby imposes a minimum height above the ground for the table. It is known for the height of a patient support table to be adjustable so that loading or unloading of a patient on or from the table can be carried out at a lower position.

Various systems for controllably adjusting the height of the patient support table are known. For example, the patient support may comprise a telescopic pedestal system for height adjustment of the table. Alternatively, a ram may be used for this height adjustment, but this requires a recess in the ground of a depth corresponding to the range of height movement of the patient support table. A further alternative comprises a scissor-jack system which avoids the need for a deep recess in the ground. However, the above systems either require complex and expensive mechanical components or require significant outlay for installation.

U.S. Pat. No. 5,149,074 discloses a patient support table which is vertically displaceable by an arrangement of two arms connected between a base and the support table, the two arms being pivotally connected to each other. To ensure vertical lifting of the patient support, the angles between the lower arm and the base, between the two arms, and between the upper arm and the patient support must each be controlled and synchronised to maintain the patient support in a horizontal plane and to ensure vertical lifting and lowering of the support. This requires numerous control mechanisms to ensure the patient support remains horizontal, and the patient support is constrained to vertical movement only.

According to a first aspect of the present invention there is provided a patient support comprising a base; a first supporting arm pivotally mounted at a first end to the base, the first supporting arm comprising linkages pivotally connected together at four points which define a first parallelogram, a first side of which is fixed relatively to the base in a predetermined orientation, a second opposite side of which, at the second end of the first supporting arm, thereby being constrained to have the same predetermined orientation; a second supporting arm pivotally mounted at a first end to the second end of the first supporting arm, and comprising linkages pivotally connected together at four points which define a second parallelogram, a first side of which, at the first end of the second supporting arm, is fixed to and has the same orientation as the second side of the first parallelogram, a second opposite side of which, at a second end of the second supporting arm, thereby being constrained to have the same orientation; a support member connected to the second end of the second arm; and a patient support table coupled to the support member, means being provided for controlling the pivotal connections between the base and the first supporting arm and between the first supporting arm and the second supporting arm.

In the support according to the first aspect of the invention, the two supporting arms each comprise linkages defining a parallelogram. In this way, it is possible to maintain the support member at a fixed orientation without the need for a specific mechanism to maintain the support member at the desired orientation. The predetermined orientation may be perpendicular to the base, in which case the patient support table may be coupled to the support member so as to be perpendicular to the second side of the second parallelogram, in order that the patient support table is maintained parallel to the base.

The first supporting arm may be mounted to the base through a rotational coupling, enabling rotation about an axis perpendicular to the base. This enables the orientation of the support member within a plane parallel to the base to be adjusted.

The control of the pivotal connection between the base and the first supporting arm may be by means of a driven actuator, and the pivotal connection between the first supporting arm and the second supporting arm may be by a passive arrangement, such that a driven change in the angle between the base and first supporting arm of a first value results in a change in the angle between the first supporting arm and the second supporting arm of twice the first value. Such an arrangement requires only a single driven actuator, and the passive arrangement ensures that the support member is moveable only linearly, and this may be desirable to ensure that there is only vertical movement of the support member. The passive arrangement may comprise meshing gears provided on the first and second supporting arms.

A driven coupling may be provided between the support member and the patient support table, so that the first and second arms enable movement of the support member in a first plane perpendicular to the base (for example vertical) and the driven coupling enables movement of the patient support table in a second plane parallel to the base (for example horizontal). This enables movement of the patient support along three orthogonal axes.

According to a second aspect of the present invention, there is a provided a patient support comprising a base; a first supporting arm pivotally mounted at a first end to the base; a second supporting arm pivotally mounted at a first end to the second end of the first supporting arm; a support member connected to the second end of the second supporting arm; means for maintaining the support member at a constant orientation relatively to the base; a patient support table coupled to the support member by a driven coupling, the first and second arms enabling movement of the support member relatively to the base in a first plane perpendicular to the base, and the driven coupling enabling movement of the patient support table relatively to the support member in a second plane parallel to the base; drive means for controlling the pivotal connection between the base and the first supporting arm and between the first supporting arm and the second supporting arm; and means for controlling the driven coupling.

The driven coupling may comprise third and fourth supporting arms pivotally connected together, or may comprise meshing gears to enable linear movement of the patient support.

The pivotal connection between the base and the first supporting arm, in a patient support according to the first or second aspect of the invention, may be controlled by means of a first driven actuator, and the pivotal connection between the first supporting arm and the second supporting arm may then be controlled by means of a second driven actuator, the actuators being independently controllable.

In this way, the first and second supporting arms enable adjustment of the position of a support member within a plane of movement, not limited to linear movement. For example, the two supporting arms may enable movement of the support member both vertically and horizontally, without the need for any articulated coupling between the support member and the patient support table (although this may be provided for additional freedom of movement).

Thus, in a third aspect of the invention, a patient support comprises; a base; a first supporting arm pivotally mounted at a first end to the base; a second supporting arm pivotally mounted at a first end to the second end of the first supporting arm; a support member connected to the second end of the second supporting arm; means for maintaining the support member at a constant orientation relatively to the base; a patient support table coupled to the support member; and first drive means for controlling the pivotal connection between the base and the first supporting arm and second drive means for controlling the pivotal connection between the first supporting arm and the second supporting arm, the first and second drive means being independently controllable.

The present invention will now be described by way of example, with reference to, and as shown in the accompanying drawings, in which.

It should of course be understood that the drawings are not to scale and that likened reference numerals are used throughout the text to refer to like parts.

Figure 1:
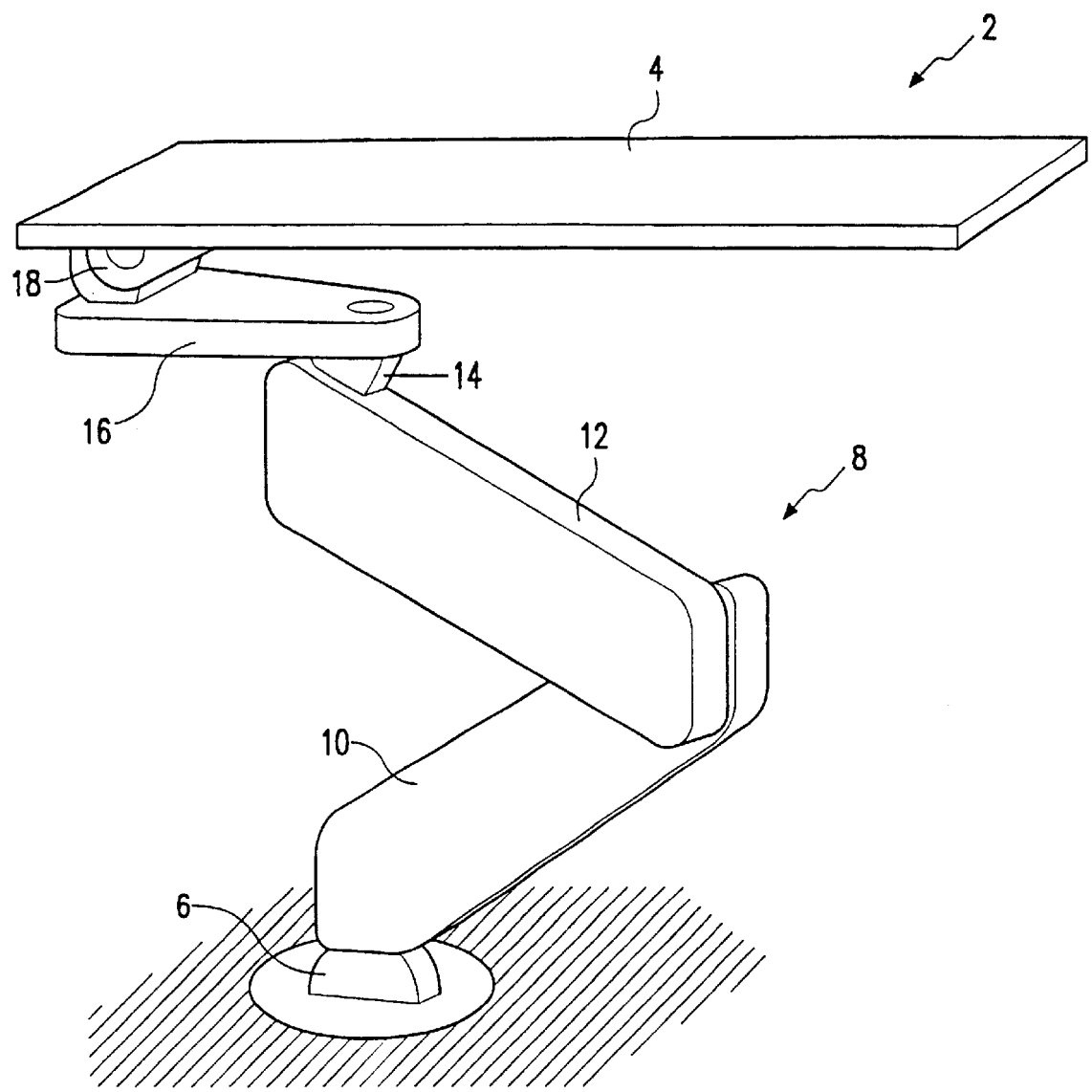
FIG. 1 shows a simplified schematic view of one example of a patient support apparatus in accordance with the invention.

FIG. 1 shows in simplified form a patient support 2 in accordance with the invention. The patient support 2 comprises a patient support table 4 which is coupled to a base 6 through an articulated lever arrangement 8, which enables the patient support table 4 to be raised and lowered relative to the base 6, and which may also provide for movement of the patient support table 4 in a horizontal plane.

The lever arrangement 8 comprises a lower arm 10 and an upper arm 12 which together enable the patient support table 4 to be raised and lowered. The lower arm 10 is pivotally connected at one end to the base 6, and is pivotally connected at its other end to one end of the upper arm 12. The other end of the upper arm 12 is pivotally connected to a support member 14.

The articulated lever arrangement 8 further comprises third and fourth arms 16, 18 connected between the support member 14 and the patient support table 4 to enable positioning of the patient support table 4 in a horizontal plane.

As will be described in the following, the patient support table 4 may be connected directly to the support member 14, and the lower arm 10 and upper arm 12 may be controlled to provide for movement of the patient support table 4 in a horizontal plane as well as for raising and lowering of the table 4.

Figure 2:
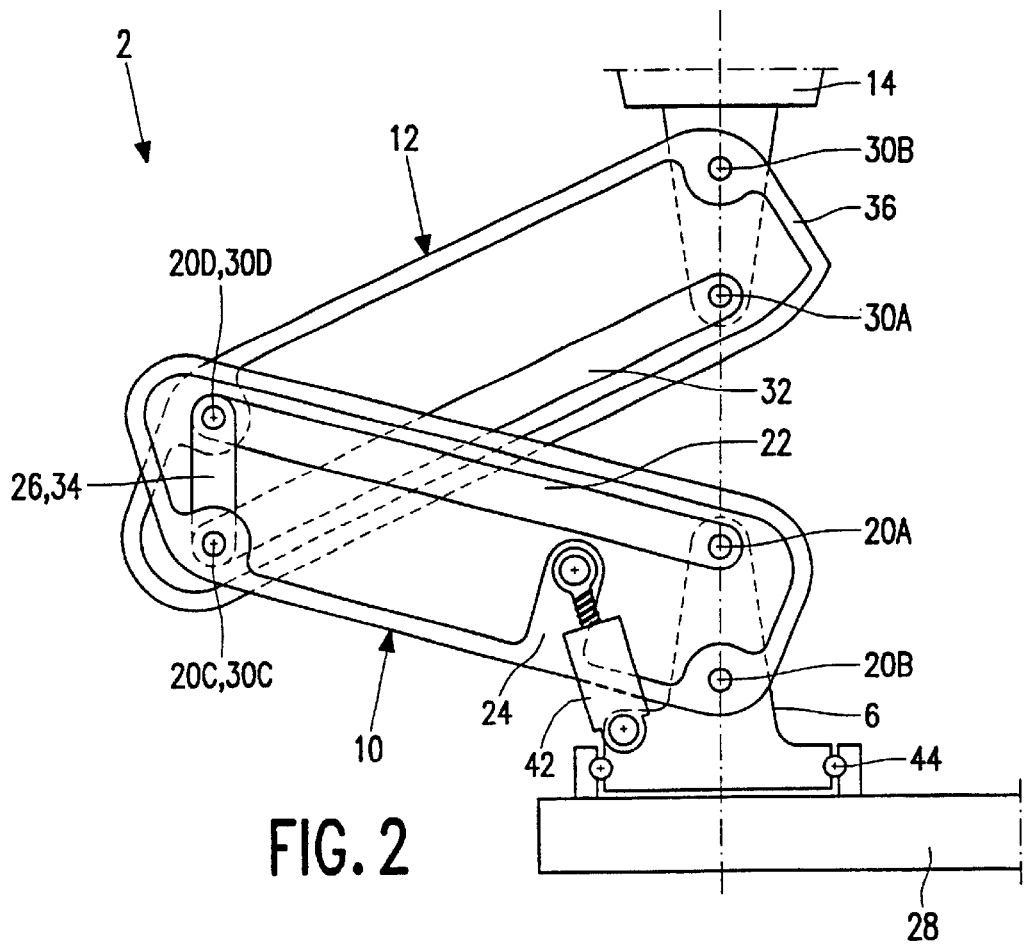
FIG. 2 shows, in greater detail, the structure of some of the components used in the apparatus of FIG. 1.

FIG. 2 shows in greater detail the construction of the upper and lower arms 12, 10. Each arm includes four pivot points and linkages connecting the pivot points so as to define a parallelogram.

Turning to the lower arm 10, the base 6 defines a first side of a parallelogram between two pivot points 20A, 20B. A lower arm linkage 22 is pivotally connected at pivot point 20A and a lower arm outer casing 24 is pivotally connected to the pivot point 20B, the casing 24 being coupled to a second lower arm linkage 26 at pivot point 20C. The two linkages 22, 26 are coupled together at pivot point 20B. In this way, the four pivot points 20A to 20D define the corners of a parallelogram, with the four sides of the parallelogram effectively defined by the two linkages 22, 26, the lower arm outer casing 24 and the base 6.

The orientation of the base 6 is constant with respect to the surface 28 to which the patient support is to be secured. The orientation between pivot points 20A and 20B is therefore constant (with respect to the base, which is positionally fixed) and this has the effect of maintaining the second lower arm linkage 26 in the same fixed orientation. The lower arm 10 is free to pivot about the base 6, and the four pivots points 20A to 20D include bearings which define the horizontal pivot axes.

The upper arm 12 comprises a similar arrangement whereby a parallelogram is defined by four pivot points 30A to 30D. As for the lower arm 10, two of the sides of the parallelogram are effectively defined by upper arm linkages 32, 34, with the other two sides effectively being defined by an upper arm outer casing 36 and the support member 14. The upper arm linkage 34 corresponds to, and has the same orientation as, the second lower arm linkage 26. In this way, the support member 14 is constrained to have the same orientation as the base 6.

In the example shown in FIG. 2, the base 6 is perpendicular to the surface 28 and therefore extends vertically, the surface normally comprising a horizontal floor. As a result, support member 14 extends vertically, and this constant orientation of the support member 14 enables the patient support table 4 to be secured to the support member 14 without the need to control any angle of tilt of the patient support table 4.

Figure 3:
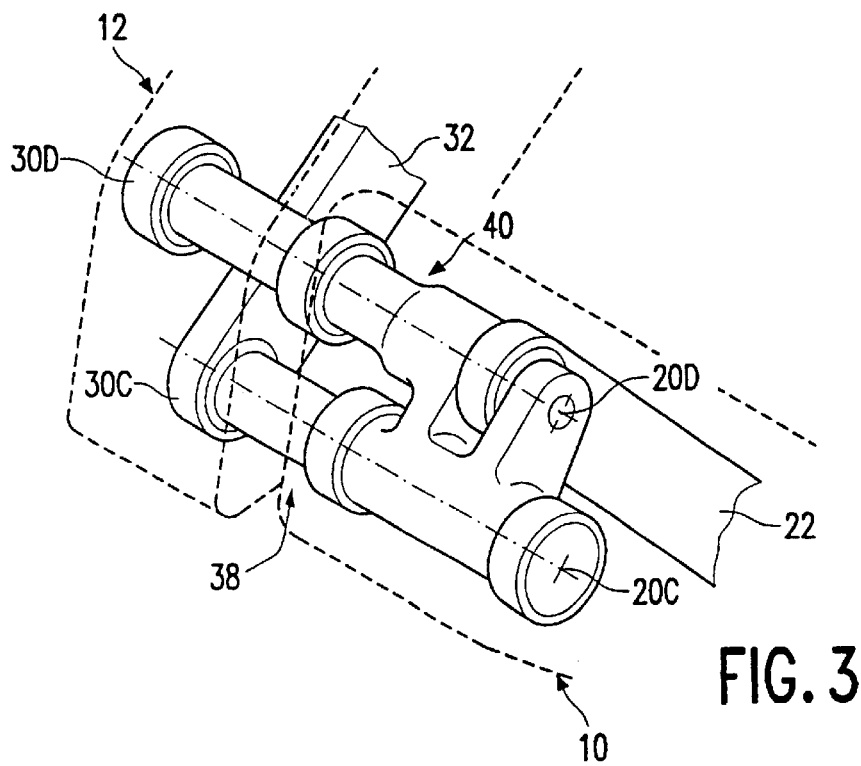
FIG. 3 shows, in greater detail, the pivotal connection between the two arms shown in FIG. 2.

FIG. 3 shows in greater detail the pivotal connection between the two arms 10, 12. As shown in FIG. 2, the linkages 26 and 34 of the upper and lower arms are aligned with the same orientation, and the pivot points are also aligned. As shown in FIG. 3, pivot points 20C, 30C are defined by a first common shaft 38 and the pivot points 20D, 30D are defined by a second common shaft 40. The arms 10, 12 are thus coupled together side by side and the arrangement of rotational bearings allows pivoting movement between the two arms.

Referring again to FIG. 2, lower arm 10 is shown to be pivoted about the pivot point 20B by a motor actuator 42 mounted on the base 6. This motor actuator may comprise a piston cylinder arrangement which may be controlled to extend and retract in order to vary the angle between the base 6 and the lower arm 10.

In a preferred embodiment of the invention, a passive arrangement ensures that the angle between the lower arm 10 and the upper arm 12 is twice the angle between the base 6 and the lower arm 10. When, as is preferred and shown in FIG. 2, the parallelograms defined by the upper and lower arms 12, 10 are identical, the angular relationship described above has the effect of aligning the support member 14 with the base 6. In this way, when the motor actuator 42 is controlled to provide lifting of the support member 14, by increasing the angle between the base 6 and the lower arm 10, the movement imparted on the support member 14 is in a vertical linear direction. FIG. 2 also shows that the complete patient support 2 may be rotated about a vertical axis with respect to the surface 28 by providing rotational bearings 44 between the base 6 and the surface 28.

Figure 4:
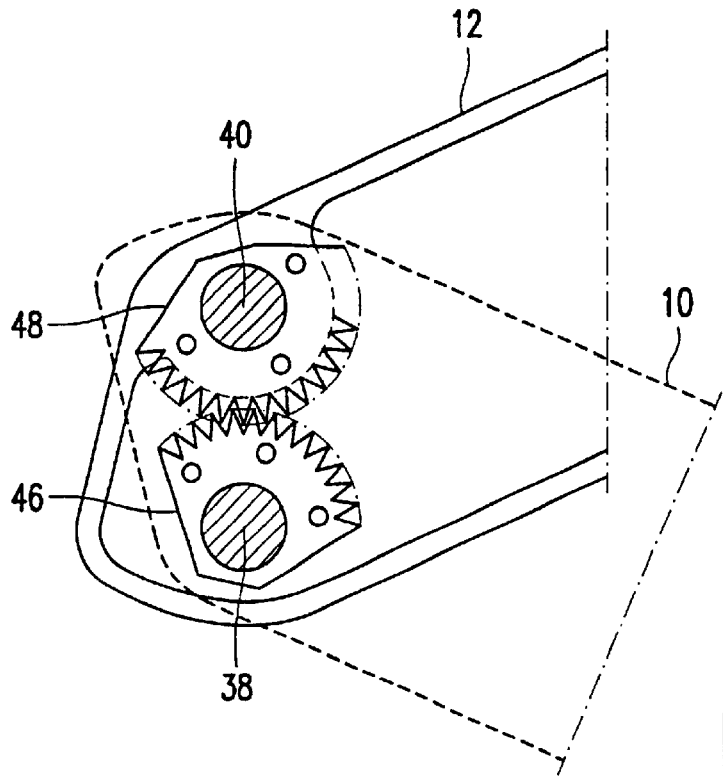
FIG. 4 shows a first alternative of controlling the angle between the two arms shown in FIG. 2.

FIG. 4 shows a first possible arrangement for controlling the angle between the upper and lower arms 12, 10 in order to achieve the vertical lifting as described. As shown, a first gearwheel 46 is associated with the lower arm 10, which meshes with a second gearwheel 48 associated with the upper arm 12. One gearwheel is mounted on the first common shaft 38 and the other gearwheel is mounted on the second common shaft 40, and each gearwheel is rotationally fixed with respect to the respective arm 10, 12. The gearwheels 46, 48 have teeth of equal pitch so that movement of the lower arm 10 by a certain angle relative to the horizontal surface 28 gives rise to an equal angular movement of the upper arm 12 with respect to the horizontal (or an angular movement between the arms 10,12 of twice the angle), thereby maintaining the support member 14 aligned with the base 6.

Figure 5:
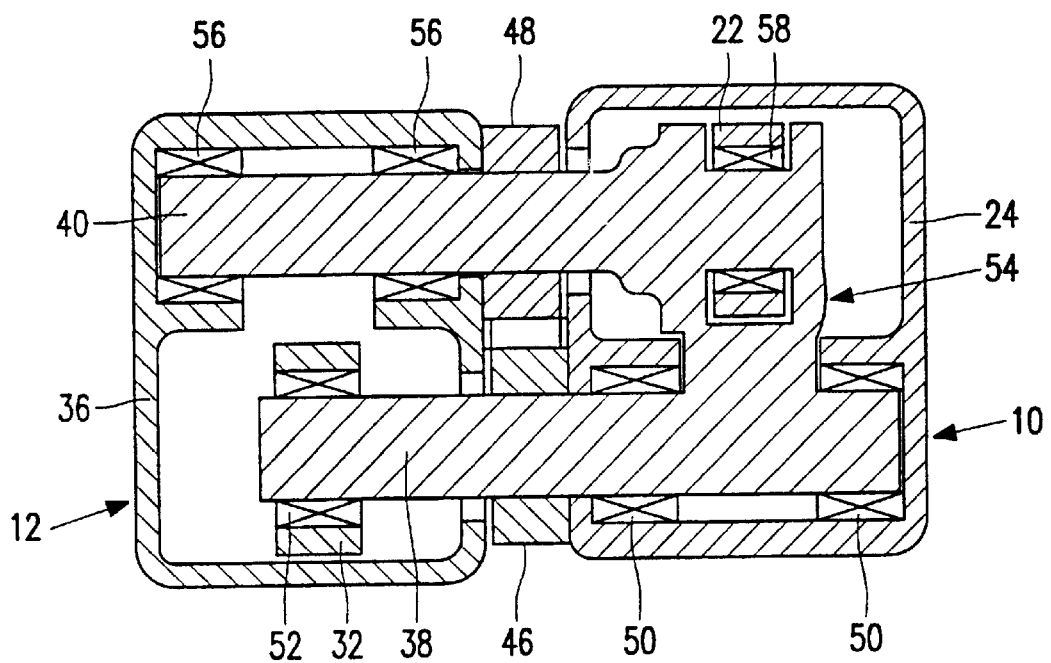
FIG. 5 shows, in greater detail, the components required for the connection shown in FIG. 4.

FIG. 5 shows the components of the linkage between the two arms 10, 12 including the gearwheel 46, 48.

The lower arm casing 24 is pivotally mounted over the first common shaft 38 by a pair of bearings 50, and the upper arm linkage 32 is also rotationally housed around the first common shaft 38 using bearings 52. The first common shaft 38 is coupled to the second common shaft 40 through a connecting region 54 which constitutes the second lower arm linkage 26 and the upper arm linkage 34. The upper arm casing 36 is rotationally supported by bearings 56 on the second common shaft 40, and the lower arm linkage 22 is also rotationally mounted around the common shaft 40 by bearings 58.

The gearwheels 46, 48 are sandwiched between the two arms 10, 12, the first gearwheel 46 being secured to the lower arm 10 and the second gearwheel 48 being secured to the upper arm 12.

Figure 6:
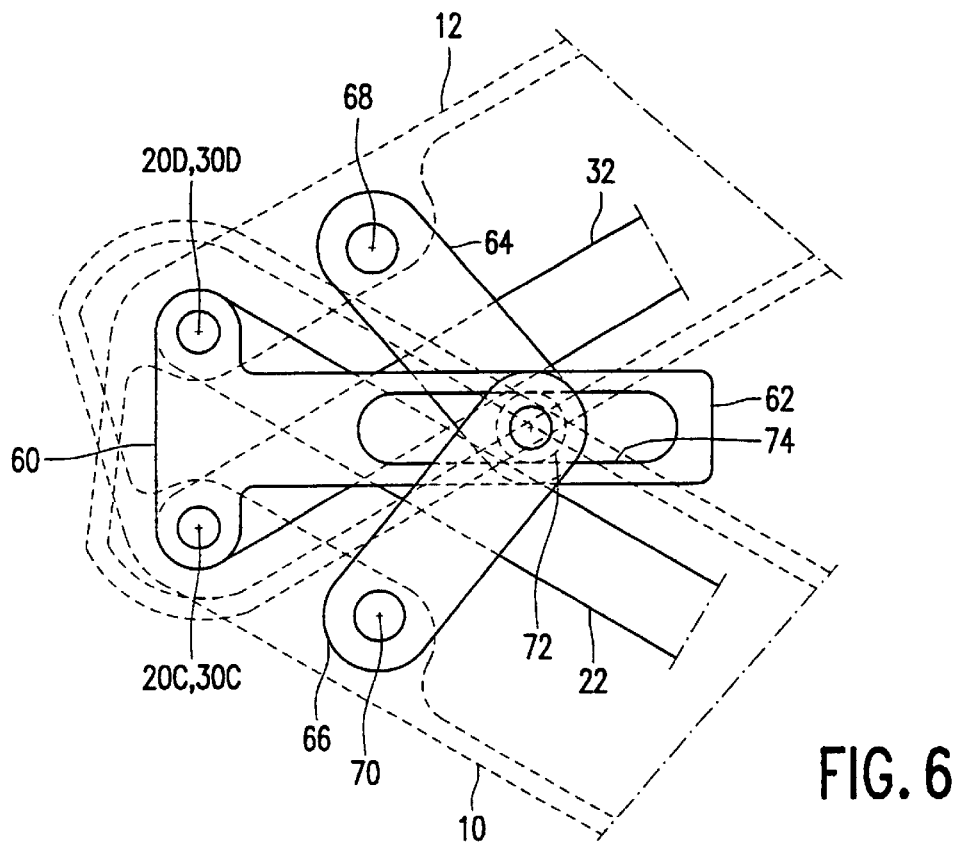
FIG. 6 shows a second alternative connection for controlling the angle between the two arms of FIG. 2.

FIG. 6 shows an alternative arrangement for producing the desired angular relationship between the upper and lower arms 12, 10, to replace the first and second gearwheels 46, 48 shows in FIGS. 4 and 5. A T-shaped member 60 defines the linkages 26, 34 of FIG. 2 which extend vertically between the pivot points 20C, 30C and 20D, 30D. The member 60 includes a horizontally extending limb 62, and the two arms 10, 12 are kept at an equal angle to the limb 62 by means of linkages 64, 66. Linkage 64 is pivotally connected to the upper arm 12 at point 68, and linkage 66 is connected to lower arm 10 at point 70. The linkages 64, and 66 have equal length and are connected together with a roller 72 which is slidable within a slot 74 provided in the limb 62. The geometric positions of the linkages 64, 66 on their respective arms are the same, so that the arms 10, 12 are constrained to be symmetrical about the limb 62.

Figure 7:
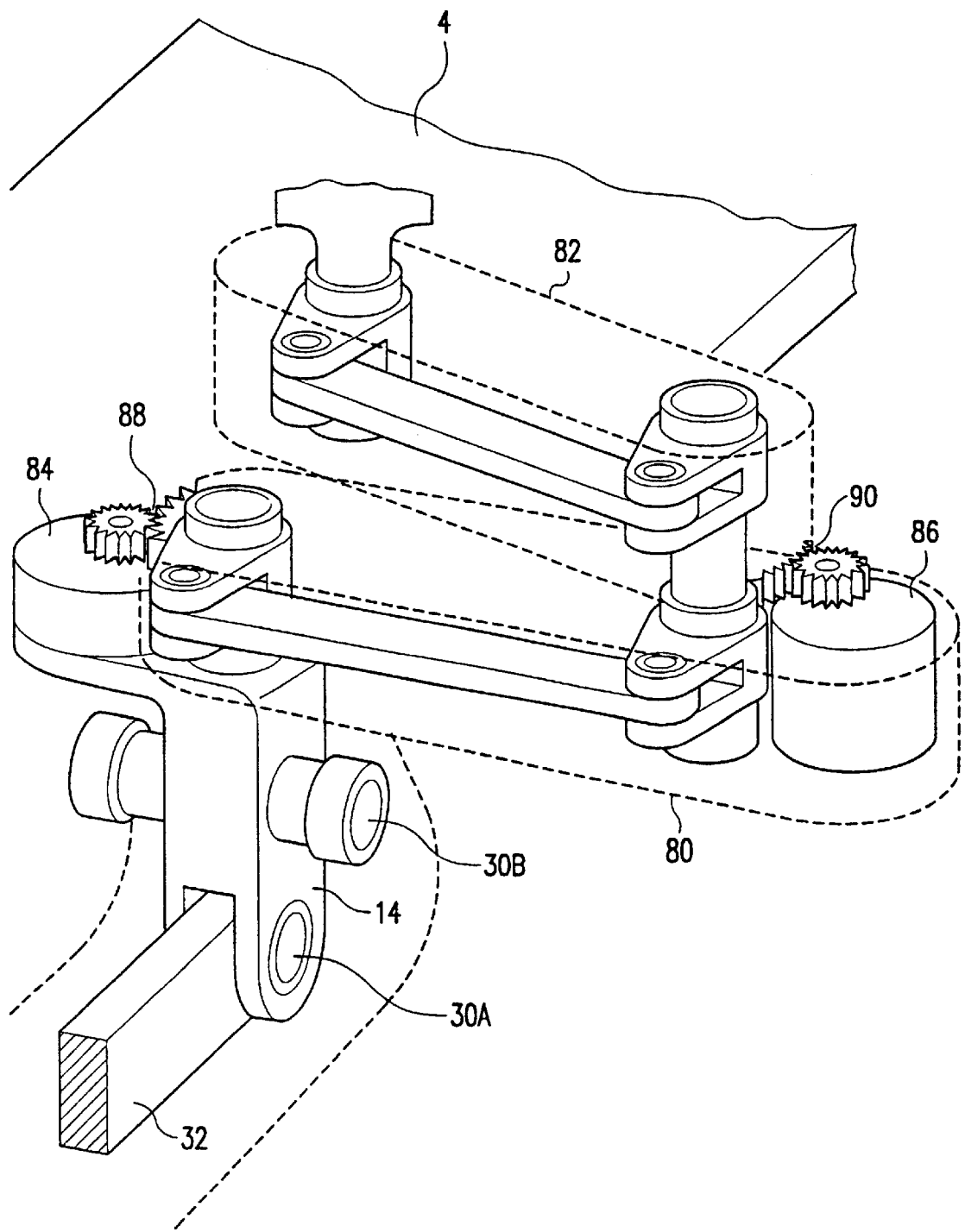
FIG. 7 shows the additional components of FIG. 1 which enable movement of the patient support in a horizontal plane.

The mechanism described in detail with reference to FIGS. 2 to 6 ensures that the support member 14 remains vertical. The patient support table 4 (shown in FIG. 1) may be mounted directly perpendicularly to the support 14 and in this way the patient support 4 is maintained horizontal during movement of the upper and lower arms 10, 12 which permit height adjustment of the table 4. However, it is preferred that the patient support table 4 is adjustable in a horizontal plane as well as having adjustable height. In FIG. 7, the patient support table 4 is connected to the support member 14 by two arms 80, 82 which may comprise similar linkages as the upper and lower arms 10, 12, thereby maintaining the movement of the patient support table 4 within the horizontal axis to a linear axis, preferably along the length of the patient support table 4. Alternatively, the arms 80, 82 may be independently controllable by respective motors 84, 86 with appropriate gearing 88, 90, as shown in FIG. 7. The arms 80, 82 may therefore be controlled to provide linear movement of the patient support table 4 along the axis of the table, or perpendicularly to the axis of the table, or along any other non-linear path.

If linear movement only of the patient support table 4 within the horizontal plane is desired, the arm linkages 80, 82 may be replaced by a rack and pinion type arrangement which enables only linear movement. Various configurations are known enabling the stepping of a patient support table along the axis of the table, to enable a patient to be stepped through a treatment or a diagnostic machine, and those skilled in the art will appreciate that any such positioning mechanism may be employed between the support member 14 and the patient support table 4.

In the example described, the upper and lower arms 10, 12 are mechanically designed so that vertical lifting and lowering of the support member 14 is provided. It is so far been described that any movement of the patient support table for in a horizontal plane should be achieved by a separate coupling mechanism between the support member 14 and the patient support table 4. However, if the angle between the lower arm 10 and the base 6 is controllable independently of the angle between the upper and lower arms 12, 10, then a limited amount of horizontal movement may also be provided by appropriate control of these angles.

Figure 8:
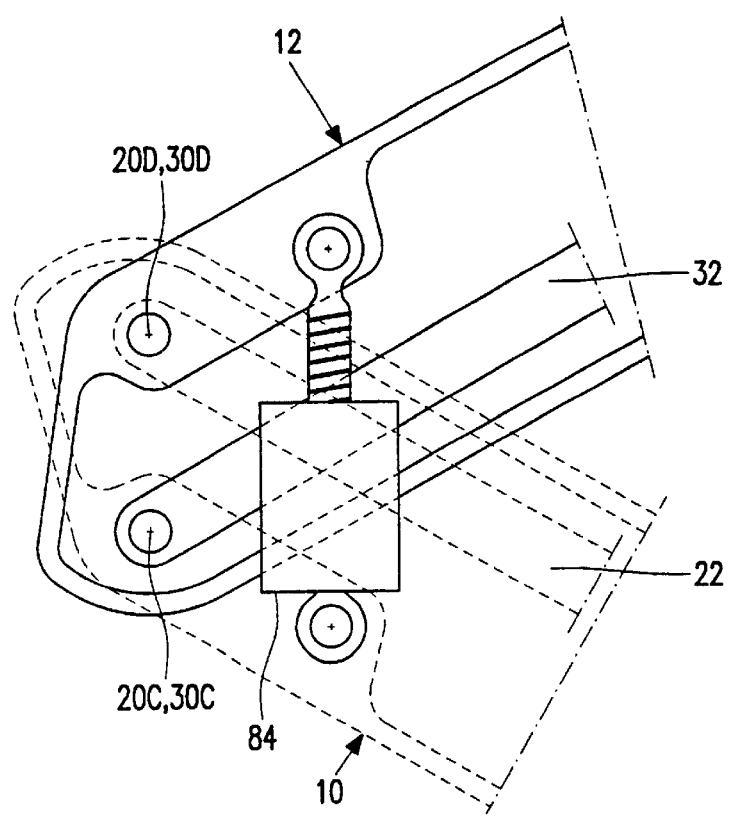
FIG. 8 shows a third alternative connection for controlling the angle between the two arms of FIG. 1.

FIG. 8 shows a motor actuator positioned between the upper and lower arms 12, 10, and which has a similar structure to the actuator 42 shown in FIG. 2. Of course, the actuator 84 controlling the angle between the upper and lower arms 12, 10 may be controlled in synchronism with the actuator 42 so as to provide vertical lifting of the patient support table 4. However, with independent control of the actuators 42, 84, it is possible to provide movement to any position within a vertical plane, within the range of reach of the arms 10, 12.

Figure 9A:
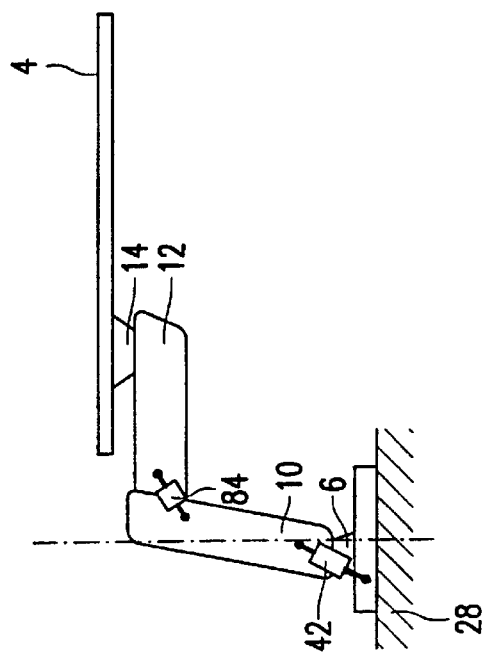
FIGS. 9A–9C shows the control possible using the system shown in FIG. 8.
Figure 9B:
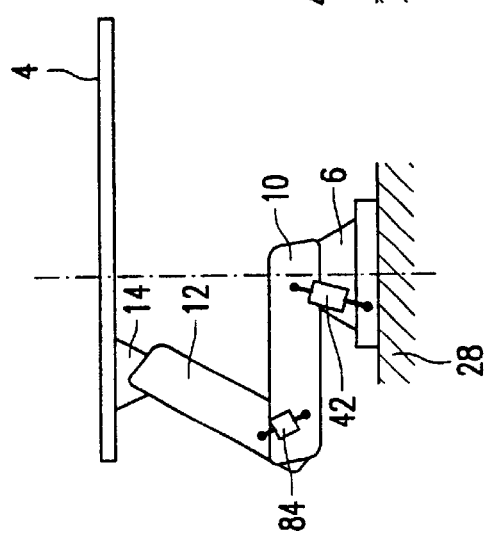
Figure 9C:
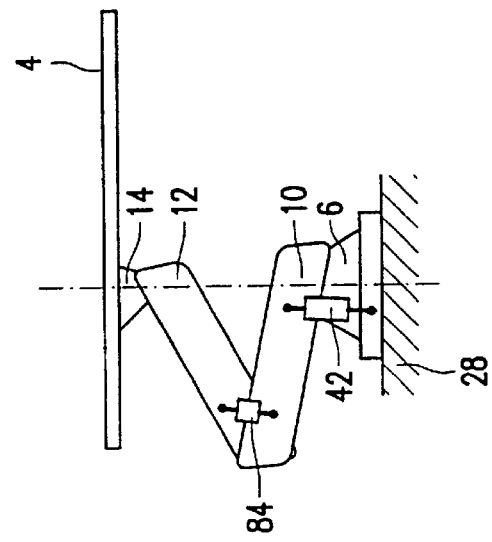

FIG. 9 shows an example of operating positions of the upper and lower arms 12, 10 to achieve movement along an axis in the horizontal plane whilst maintaining a desired height. More complicated movement may also be achieved by controlling the angular position of the base 6 with respect to the surface 28, which enables rotation of the entire patient support 2.

FIG. 9 part A shows the support member 14 and the base 6 aligned, which corresponds to normal vertical lifting of the patient support 4 as shown in FIG. 2. However, as shown in FIG. 9 part B and part C, the patient support table 4 may be maneuvered rearwardly or forwardly as desired.

In the above description, and in the claims, when components are described as having a "constant orientation" relatively to each other, this should be understood as indicating that any relative movement between the components may be defined as a linear transformation only. Similarly, reference to components having the same orientation indicates that the directions in which the components extend are parallel, although not necessarily aligned.

The references to parallelograms indicate the existence of four points connected together, for example by linkages, in such a way that joining the points with straight lines would define a parallelogram. It is not intended or required that straight couplings must be provided between the pivot points, and this is not the case in the examples described.

The coupling 16,18 has not been described in great detail. However, the skilled addressee will appreciate that some or all of the technical aspects of the arms 10,12 may be repeated in the arms 16,18, and that a totally different system for controlling the relative movement between the support member 14 and table 4 may instead be employed in those cases where such relative movement is desired.

In the preferred embodiment described, the upper and lowed arms 12,10 comprise linkages to maintain the table 4 horizontal without the need for additional control. However, some aspects of the invention do not require this configuration. Thus, where claims do not recite this particular configuration it should be understood that separate control of the angle between the upper arm 12 and the support member 14 or table 4 could be envisaged, whether as a driven actuator or as an additional passive arrangement. This separate control would then constitute means for maintaining the support member at a constant orientation relatively to the base.

In the embodiments described, the support member 14 is coupled through a mechanism to the table 4, or is attached to it. However, the support member 14 and the table 4 may, of course, together form an integral component, and the claims should be construed accordingly.

From reading the present disclosure, other modifications and variations will be apparent to persons skilled in the art. Such modifications and variations may involve equivalent features and other features which are already known in the art and which may be used instead of or in addition to features already disclosed herein. Although claims have been formulated in this Application to particular combinations of features, it should be understood that the scope of the disclosure of the present application includes any and every novel feature or any novel combination of features disclosed herein either explicitly or implicitly and any generalisation thereof, whether or not it relates to the same invention as presently claimed in any Claim and whether or not it mitigates any or all of the same technical problems as does the present invention. The Applicants hereby give notice that new claims may be formulated to such features and/or combinations of such features during prosecution of the present application or of any further application derived therefrom.

What is claimed is:

1. A patient support comprising:
    a base;
    a first supporting arm pivotally mounted at a first end to the base, the first supporting arm comprising linkages pivotally connected together at four points which define a first parallelogram, a first side of which is fixed relatively to the base in a predetermined orientation, a second opposite side of which, at the second end of the first supporting arm, thereby being constrained to have the same predetermined orientation;
    a second supporting arm pivotally mounted at a first end to the second end of the first supporting arm, and comprising linkages pivotally connected together at four points which define a second parallelogram, a first side of which, at the first end of the second supporting arm, is fixed to and has the same orientation as the second side of the first parallelogram, a second opposite side of which, at a second end of the second supporting arm, thereby being constrained to have the same orientation;
    a support member connected to the second end of the second arm; and
    a patient support table coupled to the support member, means being provided for controlling the pivotal connections between the base and the first supporting arm and between the first supporting arm and the second supporting arm.

2. A patient support as claimed in claim 1, wherein the predetermined orientation is perpendicular to the base, and wherein the patient support table is coupled to the support member so as to be perpendicular to the second side of the second parallelogram, the patient support table thereby being maintained parallel to the base.

3. A patient support as claimed in claim 2, wherein the first supporting arm is mounted to the base through a rotational coupling, enabling rotation about an axis perpendicular to the base.

4. A patient support as claimed in claim 3, wherein control of the pivotal connection between the base and the first supporting arm is by means of a driven actuator, and the pivotal connection between the first supporting arm and the second supporting arm is by means of a passive arrangement, such that a driven change in the angle between the base and first supporting arm of a first value results in a change in the angle between the first supporting arm and the second supporting arm of twice the first value.

5. A patient support as claimed in claim 4, wherein the passive arrangement comprises meshing gears provided on the first and second supporting arms.

6. A patient support as claimed in claim 2, wherein control of the pivotal connection between the base and the first supporting arm is by means of a driven actuator, and the pivotal connection between the first supporting arm and the second supporting arm is by means of a passive arrangement, such that a driven change in the angle between the base and first supporting arm of a first value results in a change in the angle between the first supporting arm and the second supporting arm of twice the first value.

7. A patient support as claimed in claim 6, wherein the passive arrangement comprises meshing gears provided on the first and second supporting arms.

8. A patient support as claimed in claim 6, wherein third and fourth sides of the first and second parallelograms are all of substantially equal length, such that the support member is movable linearly along an axis which is perpendicular to the base.

9. A patient support as claimed in claim 1, wherein the first supporting arm is mounted to the base through a rotational coupling, enabling rotation about an axis perpendicular to the base.

10. A patient support as claimed in claim 9, wherein control of the pivotal connection between the base and the first supporting arm is by means of a driven actuator, and the pivotal connection between the first supporting arm and the second supporting arm is by means of a passive arrangement, such that a driven change in the angle between the base and first supporting arm of a first value results in a change in the angle between the first supporting arm and the second supporting arm of twice the first value.

11. A patient support as claimed in claim 10, wherein the passive arrangement comprises meshing gears provided on the first and second supporting arms.

12. A patient support as claimed in claim 10, wherein third and fourth sides of the first and second parallelograms are all of substantially equal length, such that the support member is movable linearly along an axis which is perpendicular to the base.

13. A patient support as claimed in claim 1, wherein control of the pivotal connection between the base and the first supporting arm is by means of a driven actuator, and the pivotal connection between the first supporting arm and the second supporting arm is by means of a passive arrangement, such that a driven change in the angle between the base and first supporting arm of a first value results in a change in the angle between the first supporting arm and the second supporting arm of twice the first value.

14. A patient support as claimed in claim 13, wherein the passive arrangement comprises meshing gears provided on the first and second supporting arms.

15. A patient support as claimed in claim 13, wherein third and fourth sides of the first and second parallelograms are all of substantially equal length, such that the support member is movable linearly along an axis which is perpendicular to the base.

16. A patient support as claimed in claim 1, further comprising a driven coupling between the support member and the patient support table, the first and second arms enabling movement of the support member in a first plane perpendicular to the base, and the driven coupling enabling movement of the patient support table in a second plane parallel to the base.

17. A patient support as claimed in claim 16, wherein the driven coupling comprises third and fourth supporting arms pivotally connected together.

18. A patient support as claimed in claim 16, wherein the driven coupling comprises meshing gears to enable linear movement of the patient support.

19. A patient support comprising:

a base;

a first supporting arm pivotally mounted at a first end to the base;

a second supporting arm pivotally mounted at a first end to the second end of the first supporting arm;

a support member connected to the second end of the second supporting arm;

means for maintaining the support member at a constant orientation relatively to the base;

a patient support table coupled to the support member by a driven coupling, the first and second arms enabling movement of the support member relatively to the base in a first plane perpendicular to the base, and the driven coupling enabling movement of the patient support table relatively to the support member in a second plane parallel to the base; and drive means for controlling the pivotal connection between the base and the first supporting arm and between the first supporting arm and the second supporting arm, and means for controlling the driven coupling.

20. A patient support as claimed in claim 19, wherein the pivotal connection between the base and the first supporting arm is controlled by means of a first driven actuator, and the pivotal connection between the first supporting arm and the second supporting arm is controlled by means of a second driven actuator, the two actuators being independently controllable.

* * * * *

UNITED STATES PATENT AND TRADEMARK OFFICE
CERTIFICATE OF CORRECTION

PATENT NO. : 6,502,261 B1
DATED : January 7, 2003
INVENTOR(S) : William R. Harwood It is certified that error appears in the above-identified patent and that said Letters Patent is hereby corrected as shown below:

Title page,
Item [56], References Cited, U.S. PATENT DOCUMENTS, Patent No. 5,149,074, delete, "Jardin" and insert -- Jarin --

Column 2,
Line 43, before "provided" delete "a"

Column 6,
Line 29, delete "is" and insert -- has --
Line 31, after "table" delete "for"

Column 7,
Line 15, delete "lowed" and insert -- lower --

Signed and Sealed this

Thirteenth Day of April, 2004

JON W. DUDAS
*Acting Director of the United States Patent and Trademark Office*